(12) United States Patent
Cigaina

(10) Patent No.: US 6,606,518 B1
(45) Date of Patent: Aug. 12, 2003

(54) APPARATUS AND PROCESS FOR STIMULATION OF A STATE OF COMPLETE CONTINENCE IN THE NEOSPINCTER IN THE PREPARATION OF CONTINENT NEOSTOMIES

(75) Inventor: Valerio Cigaina, Treviso (IT)

(73) Assignee: Transneuronix, Inc., Mt. Arlington, NJ (US)

(*) Notice: Subject to any disclaimer, the term of this patent is extended or adjusted under 35 U.S.C. 154(b) by 0 days.

(21) Appl. No.: 09/632,834

(22) Filed: Aug. 4, 2000

(30) Foreign Application Priority Data

Aug. 6, 1999 (IT) .................................. MI99A001784

(51) Int. Cl.⁷ ................................................ A61N 1/36
(52) U.S. Cl. .......................................... 607/41; 600/29
(58) Field of Search ................................. 128/885, 897, 128/898; 600/29–31, 36, 372–373; 607/1–3, 40–41, 115–116, 133; 623/24–25, 66.1, 14.13, 23.64, 23.66, 902

(56) References Cited

U.S. PATENT DOCUMENTS

| | | |
|---|---|---|
| 2,865,376 A | 12/1958 | Pellier et al. |
| 3,760,812 A | 9/1973 | Timm et al. |
| 4,444,207 A | 4/1984 | Robicsek |
| 4,475,560 A | 10/1984 | Tarjan et al. |
| 4,524,771 A | 6/1985 | McGregor et al. |
| 4,901,722 A | 2/1990 | Noguchi |
| 5,059,207 A | 10/1991 | Shah |
| 5,100,431 A | 3/1992 | Buster et al. |
| 5,217,471 A | 6/1993 | Burkhart |
| 5,242,458 A | 9/1993 | Bendel et al. |
| 5,292,344 A | 3/1994 | Douglas |
| 5,423,872 A | 6/1995 | Cigaina |
| 5,423,876 A | 6/1995 | Camps et al. |
| 5,433,728 A | 7/1995 | Kim |
| 5,450,739 A | 9/1995 | Bogart et al. |
| 5,489,294 A | 2/1996 | McVenes et al. |
| 5,690,691 A | 11/1997 | Chen et al. |
| 5,716,385 A | * 2/1998 | Mittal et al. ................... 607/40 |
| 5,716,392 A | 2/1998 | Bourgeois et al. |
| 5,836,994 A | 11/1998 | Bourgeois |
| 5,861,014 A | 1/1999 | Familoni |
| 5,995,872 A | 11/1999 | Bourgeois |
| 6,146,391 A | 11/2000 | Cigaina |

FOREIGN PATENT DOCUMENTS

| | | |
|---|---|---|
| DE | 44 02 058 | 1/1994 |
| WO | WO 97/41921 | 11/1997 |

OTHER PUBLICATIONS

Pickerell et al., "Construction of Rectal Sphincter and Restoration of Anal Incontinenece by Transplanting Gracile Muscle: Report of 4 Cases in Children" *Ann. Surg.* 135–853 (1952).

Schmidt, "The Continent Colostomy", *World J. Surgery*, 805–808 (1982).

* cited by examiner

*Primary Examiner*—Kennedy Schaetzle
*Assistant Examiner*—Kristen Droesch
(74) *Attorney, Agent, or Firm*—Fitch, Even, Tabin & Flannery

(57) ABSTRACT

The present invention provides an apparatus and process which can stimulate a state of complete continence of the neosphincter in the preparation of continent neostomies. More specifically, the present invention provides an apparatus and process for the stimulation of a state of complete continence of the neosphincter in the preparation of continent neostomies, comprising an electrocatheter with an electrode inserted above the neostomy near, and in electrical contact with, transplanted muscle tissue (i.e., a strip of antral gastric musculature) which has been transplanted to the distal segment of the intestine or other organ where an ostomy has been created. The apparatus and process can restore the organic continence in a subject who has undergone therapeutic alteration of an indispensable segment of the visceral anatomy (i.e., the anus or the urinary bladder), thereby significantly improving quality of life.

13 Claims, 3 Drawing Sheets

APPARATUS AND PROCESS FOR STIMULATION OF A STATE OF COMPLETE CONTINENCE IN THE NEOSPINCTER IN THE PREPARATION OF CONTINENT NEOSTOMIES

RELATED APPLICATION

This application claims priority from Italian Patent Application Number IT MI 99A001784, filed Aug. 6, 1999.

FIELD OF THE INVENTION

The present invention provides an apparatus and process which can stimulate a state of complete continence of the neosphincter in the preparation of continent neostomies. More specifically, the present invention provides an apparatus and process for the stimulation of a state of complete continence of the neosphincter in the preparation of continent neostomies, comprising an electrocatheter with an electrode inserted above the neostomy near, and in electrical contact with, transplanted muscle tissue (i.e., a strip of antral gastric musculature) which has been transplanted to the distal segment of the intestine or other organ where an ostomy has been created. The apparatus and process can restore the organic continence in a subject who has undergone therapeutic alteration of an indispensable segment of the visceral anatomy (i.e., the anus or the urinary bladder), thereby significantly improving quality of life.

BACKGROUND OF THE INVENTION

The first abdominal-perineal resection for rectal neoplasm was performed by Miles in 1908. Such treatments, although justified in light of the radical nature of the underlying disease (e.g., cancer), involved extensive destruction, including the loss of the sphincter, and were generally accepted by the patient only with great reluctance. Following perineal abdominal amputation for neoplastic intestinal disease near the anus, the principal problem remains that of restoring the patient's fecal continence. In an attempt to solve this problem, surgical research has been aimed at two principal goals:

(1) reduction of the indications, even considering the serious nature of the cancer, by performing low or ultra-low resections with the help of the preparation and development of mechanical suturing technology; and (2) reconstruction of a pseudo-continent anus, possibly in the original anatomical site.

This second, and more ambitious, goal or objective (i.e., the preparation or reconstruction of a neosphincter) has been divided in recent years into two major research trends. Pickrell et al. ("Construction of Rectal Sphincter and Restoration of Anal Incontinence by Transplanting Gracile Muscle: Report of 4 Cases in Children," Ann. Surg. 135–853 (1952)) used strips of striated muscle, gracilis muscle, or more recently the major adductor for the attempted reconstruction. Shmidt ("The Continent Colostomy," World J. Surgery, 805–808 (1982)) used strips of smooth intestinal muscle.

Beyond the problems of technical implementation, there is the substantial difference in the physiological properties of the two biological materials used. The striated muscle cannot guarantee a durable contraction when needed; for this reason, additional methods of electrostimulation and biofeedback have been used to improve its resistance. Smooth muscle, on the other hand, can offer a tonic contraction for long periods of time, making it more similar to the function of the natural sphincter. In addition, even when it is denervated and devascularized, smooth muscle will not atrophy. On the contrary, it has a distinct and early tendency to create secondary revascularization, with the possibility of reinnervation as well.

This smooth muscle behavior permits a rapid resumption of its contractile activity with the appearance of a persistent and durable tonus, replaced by relaxation under the effect of substantial pressure from above. The use of smooth muscle to create a neosphincter according to Shmidt (1982) appears to be the most promising method. Indeed, the clinical results obtained are generally satisfactory in that it reasonably appears that pseudo-continence has been achieved. However, this technique does not allow for a state of complete continence, which is the optimal condition for the patient.

Thus, there remains a need for improved apparatus and procedure for stimulating or providing a state of complete continence of the neosphincter in the preparation of continent neostomies. The present invention provides such apparatus and procedure.

SUMMARY OF THE INVENTION

The present invention provides an apparatus and process which can stimulate a state of complete continence of the neosphincter in the preparation of continent neostomies. More specifically, the present invention provides an apparatus and process for the stimulation of a state of complete continence of the neosphincter in the preparation of continent neostomies, comprising transplanting muscle tissue consisting of a strip of antral gastric musculature onto the distal segment of the intestine or other organ where an neostomy has been created and implanting an electrocatheter with an electrode inserted above the neostomy near the transplanted muscle. The apparatus can completely restore the organic continence in a subject who has undergone therapeutic alteration of an indispensable segment of the visceral anatomy (i.e., the anus or the urinary bladder), thereby significantly improving quality of life.

The present invention provides a process for achieving a state of complete continence in a patient in need of a neostomy for attachment of an endoabdominal organ via an endoabdominal lumen to a neostomy site, said process comprising transplanting a strip of antral gastric musculature to the distal segment of the endoabdominal lumen adjacent to the neostomy site and implanting an electrocatheter with at least one electrode in electrical contact with the strip of antral gastric musculature, whereby stimulation of the strip of antral gastric musculature through the electrode allows generation of a reverse pressure gradient inside endoabdominal lumen and provides the state of complete continence.

The present invention also provides an apparatus for achieving a state of complete continence in a patient in need of a neostomy for attachment of an endoabdominal organ via an endoabdominal lumen to a neostomy site, said apparatus comprising an implantable electrocatheter with at least one electrode in electrical contact with a strip of antral gastric musculature transplanted to the distal segment of the endoabdominal lumen adjacent to the neostomy site, whereby stimulation of the strip of antral gastric musculature through the electrode allows generation of a reverse pressure gradient inside endoabdominal lumen and provides the state of complete continence.

The present apparatus and process use a strip of smooth muscle which is transplanted to the endoabdominal lumen attached to the neostomy. Preferably, the strip of smooth muscle is taken from about 10 cm of the small intestine which, after being prepared on the bench (i.e., ex vivo surgery), is transplanted back into the patient (i.e., autotransplanation). As compared to the known use of intestinal smooth muscle strips (i.e., the Shmidt technique), the present invention preferably involves the autotransplant of gastric antral muscle onto the distal segment of the intestine or any other organ where an ostomy has been created. Using electrostimulation from an electrocatheter with an electrode inserted above the neostomy near the transplanted muscle tissue (i.e., the transplanted strip of antral gastric musculature), the present invention allows restoration of organic continence in a subject who has undergone surgical alteration of an indispensable visceral anatomical segment, such as the anus or the urinary bladder. Thus, this invention provides an apparatus and a procedure which are suitable for the preparation of continent neostomies and are capable of guaranteeing an essentially complete state of continence.

DETAILED DESCRIPTION OF THE INVENTION

The present invention provides an apparatus and process which can stimulate a state of complete continence of the neosphincter in the preparation of continent neostomies. More specifically, the present invention provides an apparatus and process for the stimulation of a state of complete continence of the neosphincter in the preparation of continent neostomies, comprising an electrocatheter with an electrode inserted above the neostomy near the transplanted muscle tissue consisting of a strip of antral gastric musculature. The apparatus and process can completely restore the organic continence in a subject who has undergone therapeutic alteration of an indispensable segment of the visceral anatomy (i.e., the anus or the urinary bladder), thereby significantly improving quality of life.

The assumption on which the invention is based is that the gastric antral muscle is thick and is capable of effective contractile action. It also has a rich nerve supply, with neuroendocrine activity, and the removal of a small portion from the donor organ does not compromise its function. Finally, smooth muscle, even when devascularized, can take root when reimplanted in another vascularized site. The restoration of organic continence in a subject who has undergone surgical alteration of an indispensable visceral anatomical segment (e.g., the anus or the urinary bladder) is brought about, according to the invention, with an apparatus which can deliver electrostimulation to an autotransplant of antral muscle on a distal segment of the intestine or another organ where an ostomy has been created, after resection of the natural physiological orifice (e.g., anus, ureter-bladder emunctory).

Figure 1:
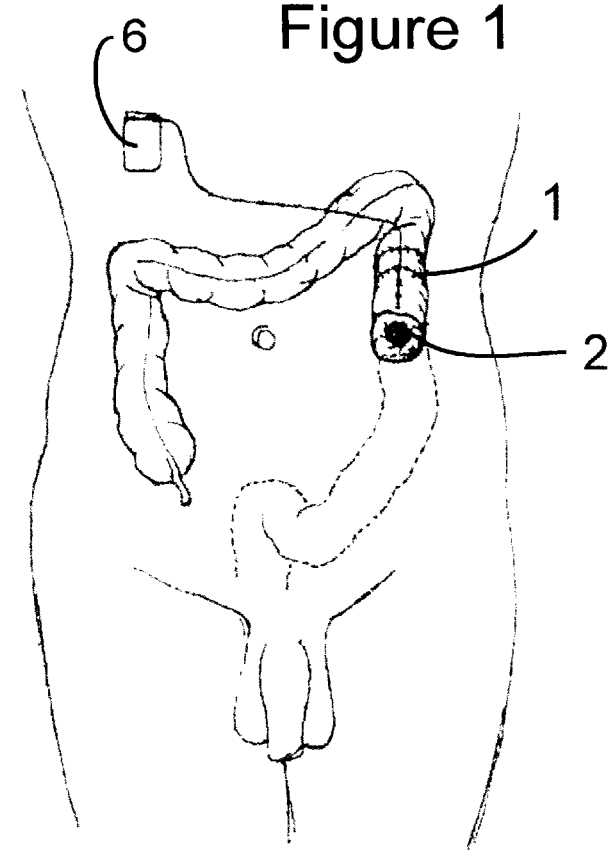
FIG. 1 illustrates the apparatus of the invention as implanted on the organ which has a neostomy created in the abdominal wall.
Figure 2:
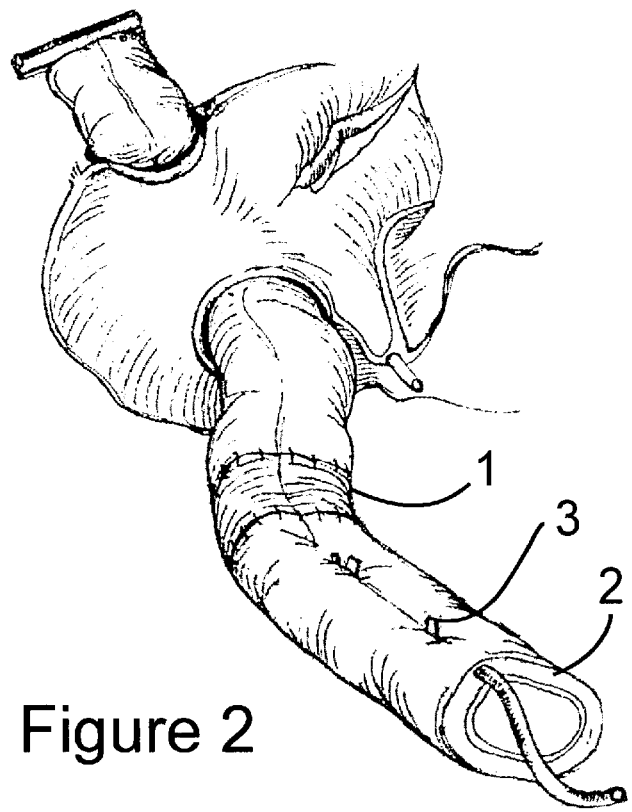
FIG. 2 illustrates the apparatus of the invention in an example of the preparation of a neostomy at the original anal site.
Figure 3:
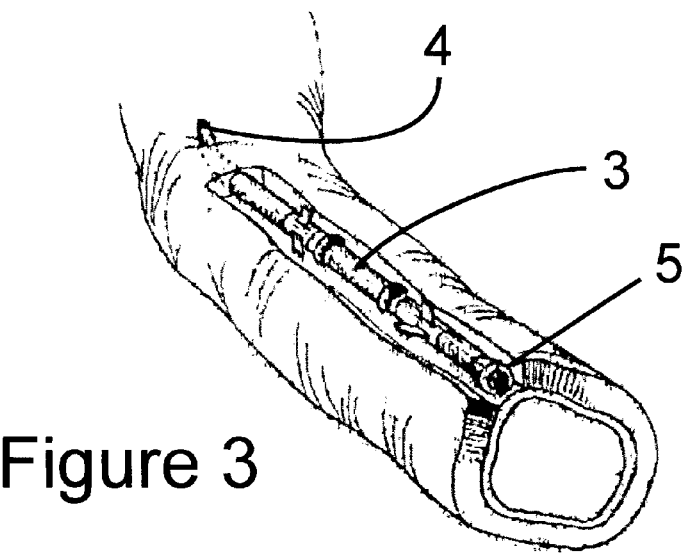
FIG. 3 illustrates the detail of the electrocatheter of the apparatus in the preceding figures.
Figure 4:
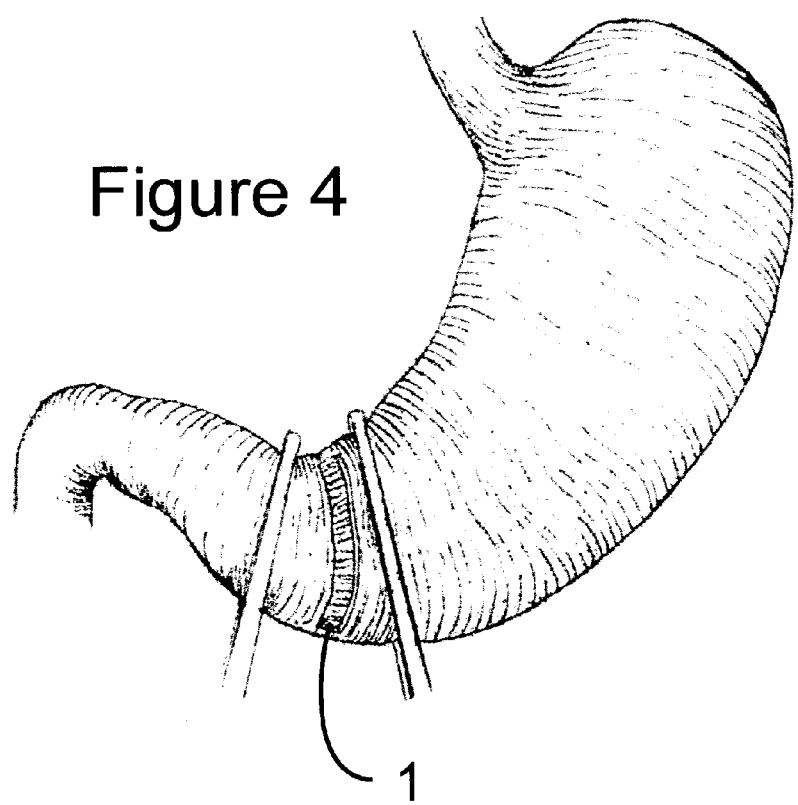
FIG. 4 illustrates the lateral view of the muscular component of the stomach.

For this purpose, a strip or ribbon 1 of gastric antral muscle is taken from the portion of the antrum where the musculature is thickest (FIG. 4). We observe that gastric resection is not necessary, so that the gastric mucosa can be left intact. This strip of antral muscle 1 will be sutured and re-implanted in the same way that it was taken from its original organ, on a circumferential or longitudinal segment of the intestinal wall near the neostomy 2, which in turn is determined by the artificial orifice created by the surgeon (neostomy on the abdominal or intergluteal wall; FIGS. 1 and 2). To this end, for a certain circumferential segment or along the larger axis of the organ for an adequate width, the most superficial serous-muscular layer will be dissected away from the deeper mucosa. The autotransplant will be completed by suturing the serous-muscular strip 1 from the gastric antrum 20 over the entire dissected segment. The apparatus of the invention is applied above this transplanted segment. The spatial relationship of the strip 1, electrocatheter 3, and neostomy 2 is best shown in FIGS. 2 and 3.

This apparatus comprises, in particular, the electrocatheter 3 illustrated in FIG. 3, which is provided with at least one needle-shaped electrode 4 which allows the catheter to be inserted into the thickness of the muscle wall, as well as a position 5 for connection to an electrostimulator 6 (FIGS. 1–3). The electrocatheter 3 may have one or more poles, depending on the type of response from the organ, and the needle 4 must be inserted above the neostomy, near the transplanted muscle tissue 1. The electrocatheter 3 follows an endoabdominal and parietal pathway consistent with its purpose.

Figure 5:
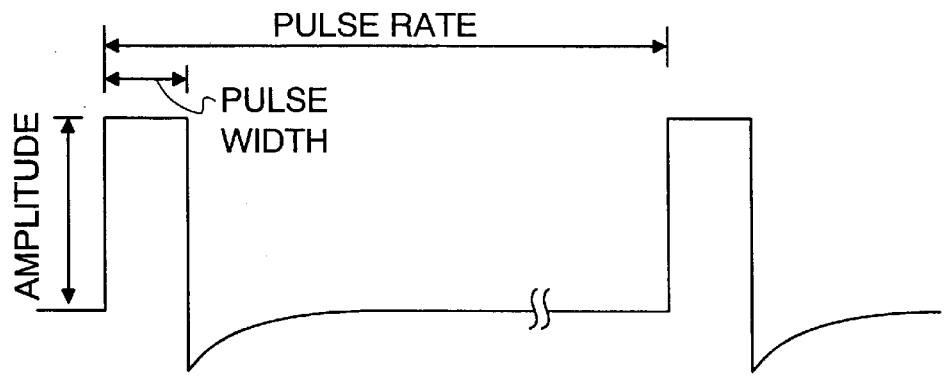
FIG. 5 illustrates the diagram of the electrical impulses provided by the electrostimulator of the apparatus of the invention.

The electrostimulator 6, which can be implanted and regulated with an external programmer, is connected under the skin of the abdominal wall in a position that is comfortable for the patient. The electrostimulator 6 can supply an electrical pulse, called a burst, in a series of electrical pulses at a certain or predetermined frequency (FIG. 5). In addition, the electrical pulse is sent continuously to the patient in the "Dosing Time ON" segment and turned off in the "Dosing Time OFF" segment (see FIG. 6). Preferably the "Dosing Time ON" and the Dosing Time OFF" are at a frequency of about 2 to about 15 per minute. Each pulse has an amplitude measured in mA or in volts, and a pulse time measured in milliseconds. The pulses are separated temporally by a frequency measured in Hertz. The table below shows typical values of the programmable parameters of the electrostimulator 6 as used in the present intention:

| Parameter | Programmable values |
| --- | --- |
| Frequency of stimulation | 1–170 Hz |
| Pulse time | 80–720 μsec |
| Pulse amplitude (stimulation current) | 0.5–18 mA (or corresponding tension in voltage output) |
| Dosing time | 1 second–24 hours |
| Therapeutic method | Automatic cycle, single cycle, or on request |

Figure 6:
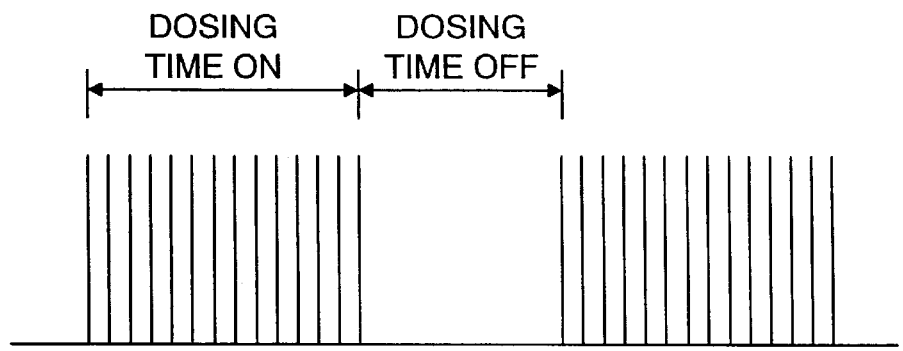
FIG. 6 illustrates the sequence of the electrical pulse generated by the electrostimulator.
Figure 7:
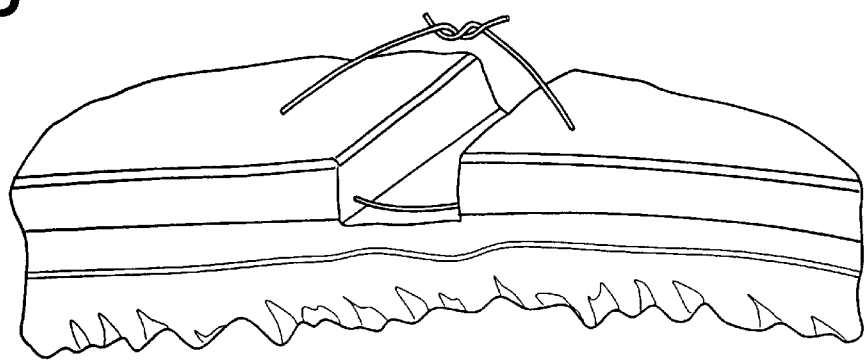
FIG. 7 illustrates the technical innovation of suturing the stomach after explant of a strip of muscle.

With regard to the therapeutic method in the above table, "automatic cycle" refers to the device supplying automatic stimulation according to the preset dosage ON/OFF time (see FIG. 6); "single cycle" refers to a device supplying stimulation which is only activated by application of an external device (e.g., magnet or other activating device); and "on request" refers to a device supplying stimulation which is started and stopped by application of an external device (e.g., magnet or other activating device).

In the digestive tract, the electrostimulated transplant has the task of reversing the pressure gradient in the tube of the organ from a cranial-caudal direction (which allows the expulsion of liquids and solid organic wastes) to caudal-cranial (with retention of these materials and temporary establishment of a "pseudo-occlusive dynamic state"). In this way, during the phase of electrical stimulation of the neostomy, it is possible to reverse, for example, the regular transit of feces. This goal can be achieved by means of the apparatus of the invention, which electrically stimulates the organ with the gastric muscle autotransplant, since the gastric muscle can support a greater contractile frequency than the intestine. In the urinary level, this principle of reversing the pressure gradient can also be valid, but here there may also be a true sphincter activity exercised by the transplant itself when it is stimulated electrically.

The electrical stimulation can be more or less effective at inducing the capture of the normal electrical/muscular activity of the internal organs with an attached muscular autotransplant, and therefore more or less capable of inducing new and higher frequency contractions. This means that it will induce an effective contraction of the transplanted muscle tissue for the purpose of performing an artificial pacesetter function, and therefore a contraction with a higher frequency than the latter intestinal segment (as compared to the intestinal segments higher up).

This procedure creates a reverse pressure gradient, and a greater downstream pressure secondary to a greater number of contractions per minute as compared to the physiological number of contractions present above, due to the natural contractile frequency of the intestine. Since there is a reverse pressure gradient in the intestinal lumen throughout the entire time of electrical stimulation, elimination of the organic material from inside the organ through the artificial anus cannot occur.

When the electrostimulator is turned off, for example, at night or other times determined by the health care provider and/or patient, the normal anterograde, or cranial-caudal pressure gradient is restored, and the organ can eliminate the organic material parked in its lumen in the right direction. This solution is enormously beneficial for the patient with an intestinal neostomy secondary to removal of the last segment of intestine with the anal sphincter for reasons of disease, because it allows the patient to have a better social life, since he can regulate the time of intestinal discharge according to his own needs and lifestyle. After an appropriate period of training concerning the intestinal functions and in relation to the electrostimulating activity, the patient will be able to avoid the use of any ostomy bag attached to the abdomen during significant periods of time (e.g., during daytime or other hours when the patient is around other people).

One way of increasing the effectiveness of the solution is to create a tunnel on the internal side of the abdominal muscle wall and below the peritoneum, through which the transplanted intestinal segment is passed with the attached stimulating electrocatheter. In this way, the electrical stimulation, by means of pulses at a frequency of 2–15 per minute can, during the adjustment phase, also cause contractions of the abdominal wall where the ostomy is located, and lead to hypertrophizing and retentive effects. Stimulation of the muscles of the abdominal well, the location of the neostomy, is secondary to the conduction of the electrical impulse from the intestine, which is in direct contact with the abdominal musculature itself. There is no reason why the neostomy cannot be created in the most comfortable position or even in the original position, which was initially sacrificed for therapeutic needs (intergluteal position).

Therefore, with the present invention, the apparatus described above guarantees essentially complete continence when it is applied above the neosphincter, to produce a reverse pressure gradient inside the secondary hollow viscus, at the highest frequency of muscle contraction provided by the autotransplant of gastric muscle.

What is claimed is:

1. A process to provide a state of complete continence in a patient in need of a neostomy for attachment of an endoabdominal organ via an endoabdominal lumen to a neostomy site, said process comprising transplanting a strip of antral gastric musculature to the distal segment of the endoabdominal lumen adjacent to the neostomy site and implanting an electrocatheter with at least one electrode in electrical contact with the strip of antral gastric musculature, whereby stimulation of the strip of antral gastric musculature through the electrode allows generation of a reverse pressure gradient inside the endoabdominal lumen and provides the state of complete continence.

2. The process as defined in claim 1, wherein the endoabdominal lumen is a portion of intestines and the strip of antral gastric musculature is obtained from the patient.

3. The process as defined in claim 1, wherein the endoabdominal lumen is a portion of urethra and the strip of antral gastric musculature is obtained from the patient.

4. The process as defined in claim 1, wherein the stimulation of the strip of antral gastric musculature is electrical.

5. The process as defined in claim 1, wherein the electrocatheter includes an electrostimulator.

6. The process as defined in claim 5, wherein the electrostimulator provides a series of electrical pulses or bursts to the strip of antral gastric musculature with a predetermined dosage time.

7. The process as defined in claim 6, wherein the series of electrical pulses or bursts has a frequency of about 1 to about 170 Hz, a pulse time of about 80 to about 720 $\mu$sec, and a pulse amplitude of about 0.5 to about 18 mA.

8. The process as defined in claim 7, wherein the predetermined dosage time is about 1 second to about 24 hours.

9. The process as defined in claim 7, wherein the electrostimulator can be adjusted to periodically interrupt delivery of the series of electrical pulses or bursts.

10. The process as defined in claim 8, wherein the electrostimulator can be adjusted to periodically interrupt delivery of the series of electrical pulses or bursts.

11. The process as defined in claim 6, wherein the electrostimulator operates using an automatic cycling procedure wherein automatic simulation is provided depending on the dosage time.

12. The process as defined in claim 6, wherein the electrostimulator operates using a single cycling procedure wherein simulation is activated using an external device.

13. The process as defined in claim 6, wherein the electrostimulator operates using an on demand cycling procedure wherein stimulation is activated and stopped using an external device.

* * * * *